(12) United States Patent
Moskal et al.

(10) Patent No.: US 12,186,124 B2
(45) Date of Patent: Jan. 7, 2025

(54) SYSTEM AND METHOD FOR TIMING CALIBRATION OF A DETECTION SYSTEM OF A TOF-PET SCANNER

(71) Applicant: UNIWERSYTET JAGIELLONSKI, Cracow (PL)

(72) Inventors: Pawel Moskal, Czulowek (PL); Kamil Dulski, Raciborz (PL)

(73) Assignee: UNIWERSYTET JAGIELLONSKI, Cracow (PL)

(*) Notice: Subject to any disclaimer, the term of this patent is extended or adjusted under 35 U.S.C. 154(b) by 206 days.

(21) Appl. No.: 18/014,195

(22) PCT Filed: Jul. 9, 2021

(86) PCT No.: PCT/EP2021/069190
§ 371 (c)(1),
(2) Date: Jan. 3, 2023

(87) PCT Pub. No.: WO2022/013105
PCT Pub. Date: Jan. 20, 2022

(65) Prior Publication Data
US 2023/0255585 A1   Aug. 17, 2023

(30) Foreign Application Priority Data
Jul. 16, 2020 (PL) .................................. 434697

(51) Int. Cl.
*A61B 6/58* (2024.01)
*G01T 1/29* (2006.01)
*G01T 7/00* (2006.01)

(52) U.S. Cl.
CPC ............ *A61B 6/585* (2013.01); *G01T 1/2985* (2013.01); *G01T 7/005* (2013.01)

(58) Field of Classification Search
CPC ........ A61B 6/585; G01T 1/2985; G01T 7/005
See application file for complete search history.

(56) References Cited

U.S. PATENT DOCUMENTS

| 6,300,026 B1 * | 10/2001 | Yamazaki ............. G03G 5/043 430/59.4 |
| 2016/0216385 A1 | 7/2016 | Moskal et al. |
| 2020/0132867 A1 | 4/2020 | Tomonori |

FOREIGN PATENT DOCUMENTS

WO    2018202787 A1   11/2018

OTHER PUBLICATIONS

Cizek J.: "PLRF Code for Decomposition of Positron Lifetime Spectra", Acta Physica Polonica A, vol. 137, No. 2. (Feb. 1, 2020) pp. 177-187, XP055847534, ISSN: 1898-794X, DOI: 10.12693/APhysPolA.137.177.

* cited by examiner

*Primary Examiner* — Hugh Maupin
(74) *Attorney, Agent, or Firm* — Rivka Friedman (57) ABSTRACT

A method and a system for a TOF-PET scanner, the TOF-PET scanner including a scintillation chamber and a detection system comprising detection modules that surround the scintillation chamber. The method includes, for each detection module being calibrated, determining distributions of lifetimes of positrons based on differences of the times of registration of annihilation quanta and of the times of registration of the de-excitation quanta assigned to the common events and registered by the module being calibrated; extracting, from the determined distributions of lifetimes of positrons, a distribution of lifetimes of positrons with annihilation by para-positronium; and determining a time delay constant based on the extracted distributions of lifetimes of positrons with annihilation by para-positronium.

11 Claims, 3 Drawing Sheets

Fig. 1A

Fig. 1B where X=X1, X2, X3..., Xm

SYSTEM AND METHOD FOR TIMING CALIBRATION OF A DETECTION SYSTEM OF A TOF-PET SCANNER

TECHNICAL FIELD

The invention relates to a system and method for timing calibration of a TOF-PET detection system installed in a PET scanner.

BACKGROUND

Images of the interior of organisms can be obtained using various types of tomographic techniques, wherein radiation from the tissues of the organism is registered and measured, and the data obtained is processed into an image.

One of the tomographic techniques includes positron emission tomography (PET), which involves determining the spatial distribution of a selected substance in the body, and makes it possible to record changes in the concentration of said substance over time, which allows for determining the rate of metabolism of individual tissue cells.

The substance of choice is a radiopharmaceutical that is administered to the patient shortly before PET imaging is performed. A radiopharmaceutical, also referred to as a radiotracer, is a chemical agent with at least one atom replaced by a radioactive isotope, such as $^{11}C$, $^{15}O$, $^{13}N$, $^{18}F$, selected so as to undergo radioactive decay while emitting a positron (an antielectron). A positron is emitted from the atomic nucleus and penetrates into the patient's tissue, where it annihilates with an electron present in the patient's body.

The electron-positron annihilation phenomenon, which is the basis of PET imaging, consists in the mass of these particles being converted into energy, which is emitted as annihilation photons, each with an energy of 511 keV. A single annihilation event usually results in two photons being created, which, in line with the law of conservation of momentum, diverge in opposite directions at an angle of 180° in the positron and electron rest system, wherein the trajectory of photon movement forming a straight line is referred to as the line of response (LOR). The stream of photons generated in the process described is referred to as gamma radiation, and each photon is referred to as a gamma quantum, so as to emphasise the nuclear origin of this type of radiation. The resulting gamma quanta have the ability to penetrate matter, including the tissues of living organisms, which allows them to be detected at a distance from the patient. The electron-positron annihilation process usually takes place within a few millimetres of where the radiotracer decays. Obviously, this fact limits the PET image resolution down to a few millimetres.

Apart from free annihilation, also referred to as direct annihilation, an annihilation of a positron with an electron in a bound state also referred to as indirect annihilation is possible. Annihilation in the bound state involves the formation of a quasi-stable state with the so-called positronium (Ps). The size of the positronium is close to that of the hydrogen atom, but the energy structure of the positronium greatly differs from that of the hydrogen atom. Both the positronium and the hydrogen atom can be formed in the singlet state with anti-parallel spins, the so-called para-positronium (p-Ps), with a mean lifetime in vacuum of $\tau_{p-Ps}$=0.125 ns or in the triplet state with parallel alignment of spins, so called ortho-positronium (o-Ps), with a mean lifetime in vacuum of $\tau_{o-Ps}$=142 ns. The o-Ps lifetime is strongly correlated with the nanostructure of the material in which the positron annihilates, varying from 0.5 ns to 142 ns. In particular, the lifetime of the ortho-positronium $\tau_{o-Ps}$ decreases to a few nanoseconds in the intercellular spaces, while in electron-dense materials such as metals, no o-Ps is generated. For the charge conjugation symmetry to be kept, p-Ps annihilates to emit an even number, usually two, of gamma quanta, while o-Ps annihilates to emit an odd number, usually three, of gamma quanta. o-Ps is three times as likely to be generated as p-Ps, wherein various interactions of the positronium with ambient electrons mean that the o-Ps to p-Ps ratio may be other than three upon annihilation. The processes leading to a change in this ratio are referred to as positronium quenching processes. One of the quenching processes includes the so-called 'pick-off' process, which involves the positron bound to an electron in the positronium annihilating with another ambient electron. This process involves the positron-electron 'bond' in the positronium being quickly broken, followed by the positron being immediately annihilated with an ambient electron. Another process leading to a shorter o-Ps lifetime is the transition of o-Ps to the p-Ps state. The probability of positronium quenching processes occurring depends on the size of the electron-free regions, wherein the larger the free spaces in the material, the less likely the quenching processes are to occur, and the longer the o-Ps lifetime.

The process of the annihilation is static in nature and is independent from the history of the annihilating positron-electron pair; accordingly, the number of annihilating positrons on the time interval dt may be expressed using the formula:

$$-dn=\lambda \cdot n(t)dt,$$

where n(t) is the number of positrons that have not annihilated by time t, $\lambda$ is the rate that characterises the positron annihilation rate in the medium.

The positron lifetime spectrum, on the other hand, is the number of positrons that have annihilated in time intervals t, t+dt, normalised to the number of total implanted positrons no. The experimentally measured positron lifetime spectrum is a combination of the theoretical spectrum function and the function describing the resolution function of the measuring apparatus, typically the Gaussian function.

Values for the mean lifetime of positrons with annihilation by a particular state (o-Ps, p-Ps) can be obtained by measuring the positron lifetime spectrum and decomposing the distribution of said lifetimes, which is the field of study of positron annihilation lifetime spectroscopy (PALS). The decomposition of the distribution of lifetimes of positrons is carried out by fitting a model that sets a known positron lifetime model against a model defining the resolution function of the apparatus used to measure PALS. The distribution of lifetimes may be used to determine parameters such as, for example, the mean lifetime of a positron with annihilation by p-Ps, the mean lifetime of a positron with annihilation by o-Ps, and the mean lifetime of a positron with direct positron-electron annihilation.

As indicated above, depending on the material in which the annihilation occurs, the mean lifetime of a positron with an intermediate o-Ps/p-Ps state of may be shortened. For o-Ps, the shortening is significant, up to hundreds of picoseconds. The mean positron lifetime for direct positron-electron annihilation is typically between 0.2 and 0.5 ns depending on the material.

The PET scanner comprises detection devices to detect gamma radiation, as well as electronics and software to determine the positron annihilation site in the body based on where and when a particular pair of gamma quanta has been detected. Radiation detectors called detection modules are usually arranged into layers forming a ring around the patient and they generally consist of inorganic scintillation material. A gamma quantum enters the scintillator, which absorbs its energy and then radiates it in the form of light (a stream of photons). The mechanism for the absorption of gamma-ray energy by the scintillator can be twofold: via the Compton effect or via the photoelectric phenomenon, with only the photoelectric effect being taken into account for calculation purposes in scanners using the PET technique. Hence, the number of photons generated in the scintillator material is assumed to be proportional to the gamma quantum energy deposited in said scintillator.

When two annihilation gamma quanta are registered by a pair of detection modules at a time interval of no more than a few nanoseconds, i.e. in the so-called coincidence, the annihilation point can be identified, which will be on the line of response LOR, i.e. on the line connecting the centres of the detectors or between points in the strip scintillators where the gamma quanta have deposited energy. The coordinates of the annihilation site are obtained from the time difference between the arrival of gamma quanta at the detectors located at the two ends of the LOR. In the literature, this technique is referred to as the time-of-flight (TOF) method, while PET scanners using time measurement are accordingly called TOF-PET. For this technique to be used, scintillators are required that have time resolution capabilities of the order of several hundred picoseconds.

Standard detection systems of PET scanners consist of a layer of scintillators surrounding a detection chamber that absorb gamma quanta from the decay of the radiopharmaceutical and emit scintillation photons. The most commonly used scintillators are inorganic crystals. Moreover, patent applications WO2011008119 and WO2011008118 disclose detection modules with polymer scintillators used in PET scanners that allow for achieving considerably improved time resolution capabilities of the detection system of the order of 100 ps.

The time resolution achieved in the detection systems of TOF-PET scanners is closely related to the spatial resolution of the reconstructed annihilation sites. Thus, improving time resolution results in an improved quality of tomographic images. The ideal feasible time resolution closely correlates with the timing calibration of all detectors of the TOF-PET scanner detection system. For timing calibration, radioactive isotopes such as $^{22}$Na or $^{68}$Ge are used, which are placed in very specific positions inside the scanner: in the scintillation chamber, for example in the geometric centre of this chamber, or in mobile settings: the radioactive isotopes are implemented as elements rotating along the ring of the scanner to allow relative synchronisation of all detection modules.

Patent literature also discloses various methods for calibrating TOF-PET scanner detection systems.

Polish patent publication PL223751 discloses a calibration method wherein cosmic radiation is used as the radiation source. The synchronisable system consists of TOF-PET scanner detectors comprising polymer strip scintillators and photoelectric converters. The method comprises registering the reaction times of cosmic ray particles with the scintillation strips of the detection modules, and determining the distributions of the pulse recording times at the ends of the scintillator connected to the photoelectric converters, which are used to determine the timing synchronisation constants of the photoelectric converters, including the delay of the electronics, the speed of light propagation in the scintillation strip of the detection module and the resolution of the time difference of the signals registered at both ends of the detection module.

Also, international patent application WO2018202878A1 discloses a method for calibrating a TOF-PET scanner detection system, wherein the calibration procedure uses a radioisotope: $^{22}$Na, K-38 or Cu-60 emitting gamma quanta, i.e. annihilation quanta with an energy of 511 keV and de-excitation quanta with an energy differing from that of the annihilation quanta, so that the detection system can make a distinction between them. The calibration is performed based on the data from the decay of said radioisotope, at a predetermined position: in the centre of the detection system. The data obtained is used to calculate the time difference ($\Delta t$) between the registration of the annihilation quantum and of the de-excitation quantum, and further calculations yield the results, which are corresponding time values: $\{t_n\}_{n=i \ldots N}$. According to this method, calibration is performed iteratively by solving a finite system of linear equations based on the time difference between the registration of a gamma quantum or quanta that originate from electron-positron annihilation, and optionally the registration of an additional gamma quantum emitted during source de-excitation. The accuracy of this method, however, depends both on the resolution of the apparatus used, and on the mean positron lifetime in the material in which annihilated took place. However, the combined factors as above increase the distribution of positron lifetime differences, resulting in increased uncertainty in the determination of relative delays between modules. Accordingly, a calibration method of this type may hinder the quality of the images reconstructed based on data from a TOF-PET scanner using the calibration method as above.

Also, patent publications U.S. Pat. Nos. 7,414,246, 78,209,075 and WO2016067150 disclose methods for timing calibration of detectors of a TOF-PET scanner detection system, wherein a sodium isotope ($^{22}$Na) placed in a shielding made of metal or plastic is used as the radiation source, while annihilation quanta scattered across the shielding are used to determine relative delays of individual detection modules of the TOF-PET system.

US patent publication U.S. Pat. No. 755,730, in turn, discloses a method for timing synchronisation of TOF-PET detectors that simultaneously uses a number radioactive sources, with the sources placed in known positions to allow the calibration to be implemented also while the patient is being scanned. Gamma quanta from calibration sources are distinguished based on the known positions of said sources and on time-related information from the detectors, which further allows for discarding the events: information on deposition of gamma quanta originating from calibration sources, so that calibration-derived quanta are not included in the tomographic image reconstruction process.

US patent publication U.S. Pat. No. 5,272,343, in turn, discloses a method for synchronising the detectors of a PET scanner detection system, wherein the orbiting of a radioactive source is used to obtain an effect similar to the calibration method using a shielding that allows synchronisation of detector pairs, determining the relative delays of the detection modules of the system.

Also, international patent application publication WO2019032911A1 discloses a method for calibrating PET detectors implemented when the patient is being scanned based on relative delays between positron emissions from the patient and positron emissions from the calibration source.

Calibration of the TOF-PET detection system is generally performed once a day before patient scans so as to prevent exposure to an additional radiation dose, which, however, prevents taking into account the changes in ambient conditions, including temperature fluctuations that affect the time- and energy-related properties of TOF-PET detectors, while also reducing the time available for patient imaging.

In addition, known methods do not allow for a sufficiently accurate calibration of the TOF-PET scanner detection modules, which may deteriorate the quality of reconstructed images obtained from the data collected by the TOF-PED scanner during scanning.

SUMMARY OF THE INVENTION

Therefore, there is a need to provide a method for calibrating detection modules of a TOF-PET scanner. Preferably, the method should allow continuous monitoring of a quality of a detection system and its simultaneous calibration (including during patient scanning), to provide improved calibration accuracy, and, as a result, more accurate timing synchronisation of the detection modules of the detection system of the TOF-PET scanner.

The object of the invention is a method for a TOF-PET scanner, the TOF-PET scanner comprising a scintillation chamber and a detection system comprising detection modules (X) that surround the scintillation chamber; the method comprising: providing a radiation source in the scintillation chamber, wherein the radiation source is configured to emit, in the scintillation chamber, both positrons for annihilation with emission of annihilation quanta and de-excitation quanta having an energy different from an energy of the annihilation quanta; registering the annihilation quanta and the de-excitation quanta deposited in the detection modules (X); selecting the registered annihilation quanta and the registered de-excitation quanta based on times of registration and energies of the deposited quanta; assigning the annihilation quanta and the de-excitation quanta to common events; the method further comprises, for each detection module (X) being calibrated: determining distributions (n=f($T_{Diff}$)) of lifetimes of positrons based on differences ($T_{Diff}$) of the times of registration of annihilation quanta ($T_{anni}$) and of the times of registration of the de-excitation quanta ($T_{deex}$) assigned to the common events and registered by the module (X) being calibrated; extracting, from the determined distributions (n=f($T_{Diff}$)) of lifetimes of positrons, a distribution (n=f($T^{(X)}_{(p-Ps)}$)) of lifetimes of positrons with annihilation by para-positronium; and determining a time delay constant ($D_{delay}^{(X)}$) based on the extracted distributions of lifetimes of positrons with annihilation by para-positronium (n=f($T^{(X)}_{(p-Ps)}$)).

Preferably, the method comprises determining the time delay constant ($D_{delay}^{(X)}$) for the detection module (X) being calibrated relative to a virtual detection module (Y) having a time delay constant ($C_{delay}^{(Y)}$) equal to an average delay value ($C_{delay}^{(average)}$) of the time delay constants of all the detection modules of the detection system, except for the detection module (X) being calibrated.

Preferably, the value of the time delay constant ($C_{delay}^{(Y)}$) of the virtual detection module (Y) is assumed to be zero.

Preferably, the method comprises determining the distributions of lifetimes of positrons for the detection module (X) being calibrated by: calculating the positron lifetime ($T_{Diff}^{(1)}$) for the events in which the detection module (X) being calibrated has registered the annihilation quantum according to the formula:

$$T_{Diff}^{(1)} = (T_{anni}^{(X)} - T_{deex}) + D_{delay}^{(X)}, \qquad \text{Formula V}$$

and calculating the positron lifetime ($T_{Diff}^{(2)}$) for the events in which the detection module (X) being calibrated has registered the de-excitation quantum according to the formula:

$$T_{Diff}^{(2)} = (T_{anni} - T_{deex}^{(X)}) - D_{delay}^{(X)}, \qquad \text{Formula VI}$$

wherein:

$T_{anni}^{(X)}$ is the time of registration of the annihilation quantum in the detection module (X) being calibrated, $T_{deex}$ is the time of registration of the de-excitation quantum originating from the common event with the annihilation quantum of the time of registration $T_{anni}^{(X)}$, $T_{deex}^{(X)}$ is the time of registration of the de-excitation quantum in the detection module (X) being calibrated, $T_{anni}$ is the time of registration of the annihilation quantum originating from the common event with the de-excitation quantum of time of registration $T_{deex}^{(X)}$, $D_{delay}^{(X)}$ is the time constant defining the delay of the detection module (X) being calibrated, and, based on the obtained calculating results, determining the distributions (n1=f($T_{Diff}^{(1)}$) and n2=f($T_{Diff}^{(2)}$)) of the lifetimes $T_{Diff}^{(1)}$ and $T_{Diff}^{(2)}$ of positrons for the detection module (X) being calibrated as a function of the number of counts n of said events.

Preferably, the method comprises determining the time delay constant ($D_{delay}^{(X)}$) of the detection module (X) being calibrated by: extracting the distributions n=f($T_{ani(p-Ps)}^{(X)}$) and n=f($T_{deex(p-Ps)}^{(X)}$) of lifetimes of positrons with annihilation by para-positronium, from the distributions (n1=f($T_{Diff}^{(1)}$) and n2=f($T_{Diff}^{(2)}$)) of lifetimes of positrons, and next, determining maxima of the extracted distributions (n=f($T_{ani(p-Ps)}^{(X)}$) and n=f($T_{deex(p-Ps)}^{(X)}$)) of lifetimes of positrons, including calculating mutual displacement of said maxima and determining a time constant defining the delay of the detection module (X) being calibrated according to the formula:

$$D_{delay}^{(X)} = \frac{\text{Max}LF_{anni}^{(X)} - \text{Max}LF_{deex}^{(X)}}{2}, \qquad \text{Formula VIII}$$

wherein:

$\text{MaxLF}_{anni}^{(X)}$ is a maximum distribution of lifetimes of p-Ps $n_1$=f($T_{ani(p-Ps)}^{(X)}$) extracted from distribution n1=f($T_{Diff}^{(1)}$), $\text{MaxL}_{deex}^{(X)}$ is a maximum distribution of lifetimes of p-Ps $n_2$=f($T_{deex(p-Ps)}^{(X)}$) extracted from n2=f($T_{Diff}^{(2)}$).

Preferably, the method the comprises carrying out the calibration of the detection system of the TOF-PET scanner with a time resolution necessary to extract the distribution of lifetimes of positrons with annihilation by p-Ps with a mean lifetime of not more than 125 ps.

Preferably, the method comprises carrying out the calibration of the detection system of the TOF-PET scanner of the time resolution of at least 100 ps.

Preferably, the method comprises carrying out the calibration of the detection system of the TOF-PET scanner comprising polymer scintillation strips as working material for deposition of annihilation and de-excitation quanta.

Preferably, the method comprises carrying out the calibration with a use of a shielding material for reducing the lifetime of positrons ($T_{Diff}$, $T_{Diff}^{(1)}$, $T_{Diff}^{(2)}$).

Preferably, the method comprises providing the radiation source in a form of at least one isotope selected from the group consisting of: $^{14}O$, $^{22}Na$ and $^{44}Sc$.

Another object of the invention is a calibration system for a TOF-PET scanner, the TOF-PET scanner comprising a scintillation chamber and a detection system comprising detection modules (X) that surround the scintillation chamber; the calibration system comprising: a radiation source for placement in the scintillation chamber, wherein the radiation source is configured to emit, in the scintillation chamber, both positrons for annihilation with emission of annihilation quanta and de-excitation quanta having an energy different from an energy of the annihilation quanta; wherein the detection system is configured to register the annihilation quanta and the de-excitation quanta deposited in the detection modules (X); a calibration module configured to select the registered annihilation quanta and the registered de-excitation quanta based on times of registration and energies pf the deposited quanta and to assign the annihilation quanta and the de-excitation quanta to common events; the calibration module is further configured to, for each detection module (X) being calibrated: determine distributions (n=f($T_{Diff}$)) of lifetimes of positrons based on a differences ($T_{Diff}$) of the times of registration of annihilation quanta ($T_{anni}$) and of times of registration of the de-excitation quanta ($T_{deex}$) assigned to the common events and registered by the module (X) being calibrated; extract, from the determined distributions (n=f($T_{Diff}$)) of lifetimes of positrons, a distribution (n=f($T^{(X)}_{(p-Ps)}$)) of lifetimes of positrons with annihilation by para-positronium; and determine a time delay constant ($D^{(X)}_{delay}$) based on the extracted distributions of lifetimes of positrons with annihilation by para-positronium (n=f($T^{(X)}_{(p-Ps)}$)).

The system and the method according to the invention relate to the timing calibration of the detection system of the TOF-PET scanner and of the calibration module by registration and selection of data describing the real world. Therefore, the presented system and method have a technical character and a technical result related to outputting processed real-world data, and therefore are not to be regarded as computer programmes as such. The invention contributes to improving the operation of the TOF-PET scanner, including in particular the detection system of said scanner, providing an improvement in the quality of the reconstructed body images of scanned patients obtained with the TOF-PET scanner, and therefore is not abstract.

BRIEF DESCRIPTION OF DRAWINGS

The object of the invention is illustrated in an embodiment in the figure, where.

DETAILED DESCRIPTION

A method has been developed to calibrate the TOF-PET scanner detection system with detection modules capable of time- and energy-based detection of gamma quanta deposited in said system. The calibration method is designed in particular for synchronising detection modules to achieve time resolution capabilities of the TOF-PET scanner below 100 ps. such as, for example, detection modules with polymer scintillation strips. The construction of such detection systems of TOF-PET scanners and of the detection modules constituting said systems, as well as their mode of operation, are known to those skilled in the art, for example from the publication of patent applications WO2011/008118 or WO2011/008119.

Herein, the terms spectrum and distribution in reference to lifetimes of positrons are used interchangeably. These terms denote the image acquired using positron annihilation lifetime spectroscopy (PALS), the image representing the distribution of the calculated time differences between the registration of the following: the radiation originating from positron annihilation, and the radiation originating from de-excitation of the radioactive isotope as a function of the number of counts (n), wherein said calculated time differences are more generally regarded as positron lifetimes. Given that said acquired images originate from spectroscopy (PALS), such images represent spectra. Thus, the spectra, i.e. the distributions acquired by PALS spectroscopy, graphically represent the correlation between of the signal intensity and the calculated differences of the times measured using the PALS technique.

Figures 1A, 1B, 1C, 1D:
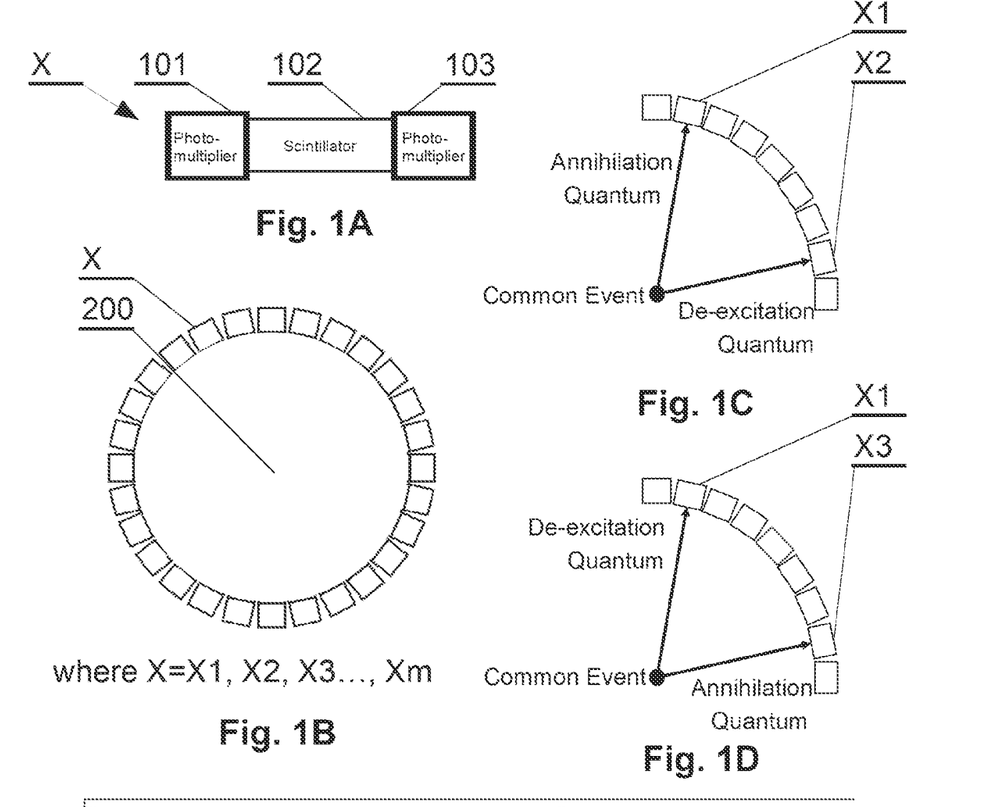
FIG. 1A is a schematic representation of a single X detection module of a TOF-PET detection system.
FIG. 1B is a schematic representation of the detection system of the TOF-PET scanner, in cross-section through the detection modules.
FIGS. 1C and 1D show a section of the detection system of FIG. 1B schematically depicting the detector pairs: X1, X2 and X1, X3, respectively, which register a pair of quanta: an annihilation quantum and a de-excitation quantum over a specified time interval.

FIG. 1A is a schematic representation of an example of a single X detector module, also referred to as a detector. The detection module X comprises a scintillation strip 102 and two photoelectric converters 101, 103, for example photomultipliers, optically connected to the ends of the scintillation strip 102. The detection module X mounted on the scanner registers the times when the light pulses generated by the gamma quanta deposited in the material of the scintillation strip 102 reached the module X, as it is the case for example in TOF-PET scanners with polymer scintillation strips known to the those skilled in the art.

FIG. 1B is a schematic cross-section representation of the detection system of a TOF-PET scanner comprising a plurality of detection modules X. In the detection system, the scintillation strips 102 are arranged parallel to each other and parallel to the longitudinal axis of the scanner to form a detection layer surrounding the scintillation chamber 200 of the TOF-PET scanner.

For example, the detector system of a TOF-PET scanner may take the form of a ring and have a circular cross-section, as shown in FIG. 1B, wherein the scintillation strips 102 are visible in cross-section; or the detector system of the TOF-PET scanner may have a different cross-section, such as oval or polygonal, as required and depending on the design requirements of the TOF-PET scanner in which the detector system is mounted. The deposition of gamma quanta in the scintillation strips 102 generates photons: light signals that propagate in opposite directions and reach the photomultipliers 101, 103, which are then converted into current signals, suitably processed by the readout electronics and stored.

The developed calibration method allows for timing synchronisation of selected detection modules, and more preferably all detection modules X of the detection system of a TOF-PET scanner in which the system is installed. Preferably, the calibration can be performed during the scanning of the patient, which provides better quality of the images reconstructed from the scanning data, since the time-related parameters of said data are subject to a calibration correction, based on the obtained values of the calibration constants. Furthermore, the inventive calibration method can also be carried out between patient scans, as required.

In the developed calibration method, chosen, i.e. appropriately selected, gamma quanta from the radiation source are registered. The inventive method uses a radioisotope as a radiation source in which the atomic nucleus undergoes radioactive decay to emit an annihilating positron, resulting in an emission of an annihilation quanta, i.e. gamma quanta with an energy of 511 keV, and at least one de-excitation quantum, i.e. a quantum with an energy other than 511 keV, preferably a de-excitation quantum with an energy much higher than 511 keV.

For example, $\beta^+$ decay radioisotopes can be used for calibration, which, once the positron is emitted, transform into excited nuclei, de-exciting by the emission of one or more gamma quanta, wherein the lifetime of the excited nucleus of the radioisotope does not exceed 100 ps, in correlation with the time resolution of the TOF-PET scanner. An example of a radiation source meeting the above criteria is the isotope of oxygen: $^{14}O$, which, upon emitting a positron, transforms into an isotope of nitrogen: $^{14}N$ in the excited state with an energy of about 2.3 MeV and an mean lifetime of about 0.07 ps, or the sodium isotope $^{22}Na$, which, by way of $\beta^+$ decay, is transformed into an excited nucleus: $^{22}Ne$ that de-excites after 3.7 ps to emit a quantum with an energy of 1.27 MeV, or the isotope $^{44}Sc$, which, as a result of radioactive decay, is transformed into an excited nucleus $^{44}Ca$ that de-excites to emit a quantum, namely a photon with an energy of 1.16 MeV after 2.6 ps, with the isotope $^{44}Sc$ being used in PET imaging.

The developed calibration method uses time and energy data from the deposition, i.e. registration of annihilation and de-excitation quanta, used to determine the de-excitation and annihilation indicators and to obtain the distributions of lifetimes of positrons, which, following their decomposition, are broken down into components in order to separate the component representing the lifetime of positrons with annihilation by p-Ps. Example data obtained by decomposing the distributions of lifetimes of positrons are shown schematically in FIG. 2, where each curve represents one extracted distribution of lifetimes of positrons. Thus, the extracted distributions originate from different modes, i.e. types of positron and electron annihilation (annihilation by o-Ps, by p-Ps or direct annihilation, respectively)—based on registered annihilation and de-excitation quanta, i.e. quanta resulting from annihilation of positron with electron and those resulting from de-excitation of radioisotope, for each pair of modules X1 and X2 of the detection system, which registered quanta originating from the common event.

Figure 3:
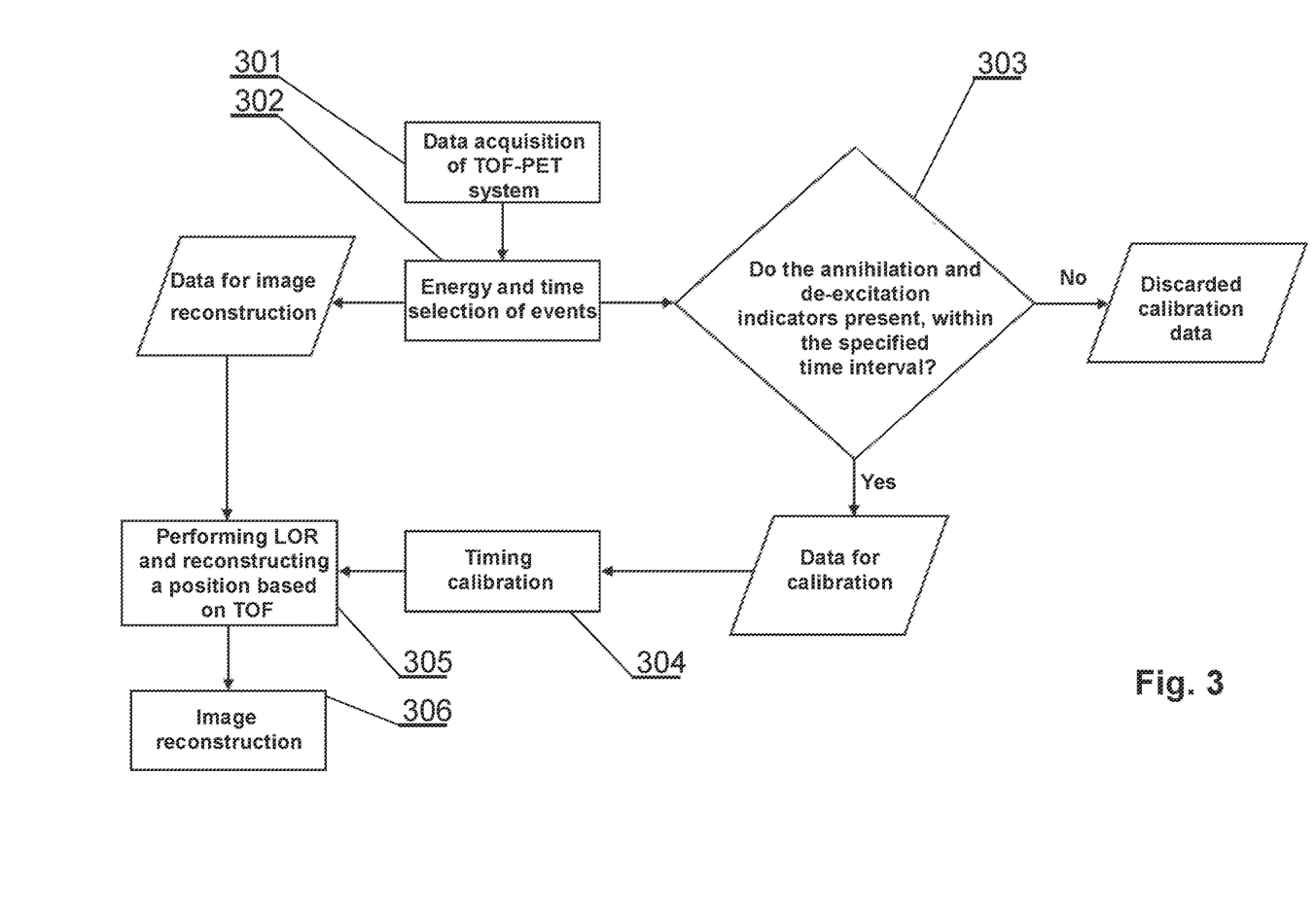
FIG. 3 is a schematic representation of the timing calibration procedure of the TOF-PET detection system.

The developed calibration method is schematically shown in FIG. 3. The method comprises:
- data acquisition in step 301, which comprises time and energy registration of gamma quanta, including annihilation and de-excitation quanta by the modules X of the TOF-PET scanner detection system,
- energy and time selection of events in step 302; wherein said step involves distinguishing signals from annihilation quanta with an energy of 511 keV from signals from de-excitation quanta with an energy other than 511 keV, wherein the energy value of the deposited de-excitation quanta is known and it depends on the radioisotope used for calibration, which is the radiation source; wherein the radiation source used for calibration may be a radiopharmaceutical administered to the patient where it is an isotope that decays to emit a positron and a de-excitation quantum, as discussed above, in which case the registered data of the signals from the annihilation quanta may be used for both calibration and reconstruction of PET images of the scanned patient; optionally, a separate radiation source, other than the radiopharmaceutical administered to the patient, may be used for calibration, in which case the signals originating from the deposition of gamma quanta resulting from the patient receiving the radiopharmaceutical are used for the reconstruction of the patient's body images, while the signals originating from the calibration quanta are used to calibrate the detection system of the TOF-PET scanner, in which case these two types of gamma quanta are selected based on a known position (point) of the calibration radiation source which does not overlap with the emission region of the positrons from the body of the scanned patient; the differences in the deposition times between the two annihilation quanta may be used to reconstruct the annihilation position along a line: LOR, which constitutes a good approximation (ensuring good quality of reconstructed images) of the positron emission site from the radiopharmaceutical, which also constitutes a good approximation of the emission site of the de-excitation quantum. Then, knowing the de-excitation and annihilation positions, it is possible to determine the time of positron emission with fair precision, i.e. so as to ensure sufficient measurement quality. Timing correlation between positron annihilation and emission thereof is used for calibration, and therefore the registered data are identified by assigning gamma quanta from annihilation and de-excitation derived from processes with the same positron, and therefore based on the site of positron emission and annihilation and of the emission of the de-excitation quantum, as well as the time of registration of said events in a predetermined common time interval, using this to assign the respective annihilation quanta and the de-excitation quantum to one (common) event;
- in step 303, calibration quanta undergo further selection: out of the data obtained, only data on events involving an annihilation and a de-excitation quanta are used for calibration, i.e. data regarding events in which during a predetermined time interval a positron, followed by de-excitation quantum, was emitted from the radiation source, wherein the time interval as above is established based on the mean positron lifetime in the material in which the positron annihilates, such as in the patient's body, and the predicted, i.e. estimated delays of modules of the detection system of the TOF-PET scanner, which is being calibrated; where the predicted delay is less than the longest lifetime of the positron in the material, the assumed time interval should be a multiple of the longest mean o-Ps lifetime: for example, the assumed time interval may be 5-fold the longest mean o-Ps lifetime in the positron annihilation material; the time interval thus selected allows for the fullest possible distribution of lifetimes of positrons to be observed and registered since it is subsequently decomposed into individual components, including the component derived from p-Ps (i.e. with the shortest positron lifetime). For biological samples such as a patient's body, it is estimated that the longest lifetime is a few nanoseconds, typically about 2 ns. Then, where the estimated delay of the modules of the TOF-PET scanner detection system can be longer than the mean positron lifetime, the time interval for registration of events is selected so as to cover the difference in maximum delays;

then, in step 304, selected data regarding events involving an annihilation and a de-excitation quantum are used for calibration calculations to obtain timing calibration constants for each module X of the detection system of the TOF-PET scanner;

while in step 305 the obtained calibration constants are employed for the reconstruction of the images of the scanned patient: for performing LOR (Line of Response) and reconstructing a position based on TOF (Time of Flight);

then, in step 306, based on the above data taking into account the obtained calibration constants, the images of the scanned patient are reconstructed.

Thus, the developed calibration method allows for calibration to be carried out in real scanning time and the calculated calibration constants to be taken into account when reconstructing PET scans, resulting in greater level of detail of images of the patient's body. Moreover, the inventive method, due to the data used for the calculation, provides greater accuracy of the calibration constants obtained, as discussed in more detail below.

The timing calibration of the modules X, of the detection system, where X=X1, X2, X3, . . . Xm, carried out in step 304 comprises calculations, for each pair of modules X1 and X2 and for each individual module X within the pair: X1, X2, wherein said calculations are identically repeated for each pair X1, X2 and each module X of said pair in order to calibrate all modules X, i.e. modules X1 to Xm of the detection system of the TOF-PET scanner.

For each pair of modules: X1 and X2, which registered during a predetermined time interval an event involving annihilation and de-excitation quanta emitted by the excited nucleus of the radiation source, as schematically shown in FIG. 1B, the difference of the times of registration $T_{Diff}$ of said quanta is calculated according to Formula I:

$$T_{Diff} = T_{anni} - T_{deex} \qquad \text{Formula I}$$

where:
$T_{anni}$—time of registration of the annihilation quantum in module X1
$T_{deex}$—time of registration of the de-excitation quantum in module X2
$T_{Diff}$—difference of the times measured by modules X1 and X2 during the predetermined time interval.

The value of the difference of times of registration $T_{Diff}$ of said quanta is an approximation of the lifetime of a single positron, and the distributions obtained in subsequent steps: $n=f(T_{Diff})$, where n is the number of registered events (number of counts), are accordingly referred to as distributions of lifetime of positrons. Distributions of lifetimes of positrons are a compilation of lifetimes of all types of positrons: those with direct annihilation, with annihilation by o-Ps and with annihilation by p-Ps. Since there are the significant differences in said lifetimes, of about 0.5 to 140 ns, the obtained distributions $T_{Diff}$ are therefore decomposed into components derived from different types of annihilation: by p-Ps, by direct annihilation and by o-Ps.

For each module X being calibrated from a given pair of modules: X1 and X2, the time of registration of the gamma quantum (annihilation or de-excitation one, respectively) measured by said module X may be expressed using Formula II:

$$t_{measured}^{(X)} = t_{calibrated}^{(X)} + C_{delay} \qquad \text{Formula II}$$

where:
$t_{measured}^{(X)}$—time of registration of the gamma quantum measured by the module X being calibrated in which said quantum has been deposited,
$t_{calibrated}^{(X)}$—the time measured by the module that is not delayed with respect to the other modules at the time of registration of the gamma quantum by the module X being calibrated (i.e. the time (time value) that should be measured by the module X being calibrated if it operated properly, i.e. without delay)
$C_{delay}$—time constant defining the delay of module X.

Two types of distributions of lifetimes of positrons can therefore be carried out for the module X being calibrated, namely for events in which:

1) the annihilation quantum will be registered by module X, and
2) the de-excitation quantum will be registered by module X.

For events falling under point 1 above, namely those for which the module X has registered an annihilation quantum, the distribution of lifetimes of positron $n_1 = f(T_{Diff}^{(1)})$, taking into account Formula I and Formula II, will be composed of times calculated according to Formula III:

$$T_{Diff}^{(1)} = (T_{anni}^{(X)} + C_{Delay}^{(X)}) - (T_{deex}^{(average)} + C_{delay}^{(average)}) \qquad \text{Formula III}$$

where:
$T_{Diff}^{(1)}$—positron lifetime for events in which the detector module X being calibrated has registered an annihilation quantum,
$T_{anni}^{(X)}$—time of registering of the annihilation quantum as measured by module X,
$C_{delay}^{(X)}$—time constant defining the delay of detector X,
$T_{deex}^{(average)}$—the averaged time of registering of the de-excitation quantum, measured by all modules that have registered the de-excitation quantum, during a single time interval (determined at the beginning of the analysis, as described above),
$C_{delay}^{(average)}$—time constant representing the average delay of all the modules, in a single time delay interval, except for the module X being calibrated.

Furthermore, when considering a virtual (theoretical) module Y whose delay constant $C_{delay}^{(Y)}$ is equal to the average value from the time constants of all modules $C_{delay}^{(average)}$, except for the module X being calibrated, and therefore when equation (Formula IV) below is true:

$$C_{delay}^{(Y)} = C_{delay}^{(average)} \qquad \text{Formula IV}$$

A virtual (theoretical) reference module is also considered with the delay constant of zero: $C_{delay}^{(Y)} = 0$, in which case the equation according to Formula III may be expressed as:

$$T_{Diff}^{(1)} = (T_{anni}^{(X)} + D_{delay}^{(X)}) - T_{deex} = (T_{anni}^{(X)} - T_{deex}) + D_{delay}^{(X)} \qquad \text{Formula V}$$

where:
$T_{Diff}^{(1)}$—positron lifetime for events in which the detector module X being calibrated has registered an annihilation quantum (thus, for the example of FIG. 1C it will be module X1), $T_{anni}^{(X)}$—time of registration of the annihilation quantum in the module X being calibrated (for the example of FIG. 1C it will be module X1), $D_{delay}^{(X)}$—the time constant defining the delay of the module X being calibrated, $T_{deex}$—time of registration of the de-excitation quantum originating from a common event with an annihilation quantum with time of registration $T_{anni}^{(X)}$ (for the example of FIG. 1C will be module X2)

As with Formula V, the lifetimes of the positrons are also determined as in point 2 above: $T_{Diff}^{(2)}$—based on timing data of de-excitation quanta registered by the module X being calibrated, according to Formula VI:

$$T_{Diff}^{(2)} = (T_{anni} - T_{deex}^{(X)}) - D_{delay}^{(X)} \qquad \text{Formula VI}$$

where:

$T_{Diff}^{(2)}$—positron lifetime for events in which the detector module X being calibrated has registered a de-excitation quantum, $T_{deex}^{(X)}$—recording time of the de-excitation quantum in the module X being calibrated (for the example of FIG. 1D it will be module X1);

$T_{anni}$—recording time of the annihilation quantum originating from a common event with a de-excitation quantum with time of registration $T_{deex}^{(X)}$, for the example of FIG. 1D it will be module X3)

$D_{delay}^{(X)}$—time constant defining the delay of the module X being calibrated Thus, the calculated positron lifetimes $T_{Diff}^{(1)}$ and $T_{Diff}^{(2)}$ relate to the same module X being calibrated, wherein lifetimes $T_{Diff}^{(1)}$ are calculated from the events in which the module X being calibrated recorded an annihilation quantum, and lifetimes $T_{Diff}^{(2)}$ are calculated from the events in which the module X being calibrated recorded a de-excitation quantum, and the recording of these events can preferably cover the entire calibration period.

Thus, $n_1$ and $n_2$ (number of counts) may be different from each other since, for a module X being calibrated, the number of counts $n_1$, for events in which said module (X) has recorded an annihilation quantum ($T_{Diff}^{(1)}$), may be other than the number of counts $n_2$ for events in which said module (X) has recorded a de-excitation quantum ($T_{Diff}^{(2)}$).

Based on the obtained results of calculations according to Formula V and Formula VI, distributions of lifetimes of positrons are carried out: number of counts n as a function of positron lifetime: $n_1=f(T_{Diff}^{(1)})$ and $n_2=f(T_{Diff}^{(2)})$, for module X being calibrated said distributions are shifted with respect to each other by a constant $D_{delay}^{(X)}$, whose value depends on relative of module X being calibrated. Nevertheless, said shift, i.e. a value of $D_{delay}^{(X)}$ for distribution of $T_{Diff}^{(1)}$ is in the direction opposite to that of to the shift for the distribution of $T_{Diff}^{(2)}$. Thus, the resulting distributions $n_1=f(T_{Diff}^{(1)})$ and $n_2=f(T_{Diff}^{(2)})$, will be shifted in relation to each other along the x-axis by a value equal to twice the constant $D_{delay}^{(X)}$ ($2 \cdot D_{delay}^{(X)}$).

Accordingly, a constant $D_{delay}^{(X)}$ is determined for each module X being calibrated, that is exclusively based on the calculated positron lifetimes: $T_{Diff}^{(1)}$ and $T_{Diff}^{(2)}$ for said module X. Namely, decomposed distributions $n_1=f(T_{Diff}^{(1)})$ and $n_2=f(T_{Diff}^{(2)})$, (according to Formula V and Formula VI) are used to extract distributions of lifetimes of positrons with annihilation by p-Ps, i.e. distributions of lifetimes of positron with annihilation by para-positronium. Such extraction can be performed using the PALS method, for example as described in A. Akmalova et al., KnE Energy & Physics, pages 1-9. DOI 10.18502/ken.v3i2.1784, or in publication: J. Cizek, Acta Physics Polon. A 137, no. 2 (2020) DOI: 10.12693/APhysPolA.137.177.

Figure 2:
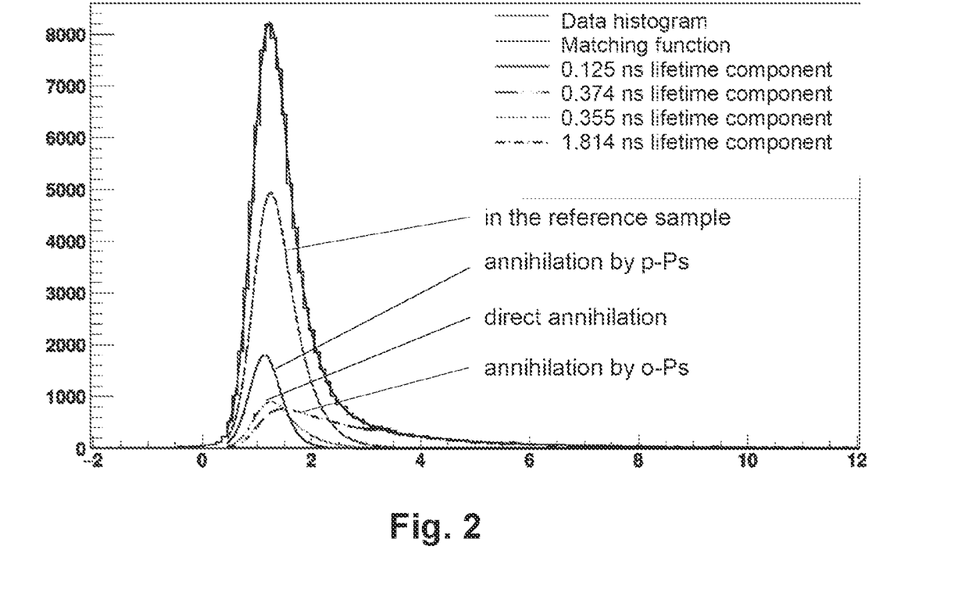
FIG. 2 shows distributions of lifetimes of positrons, decomposed into four components: the distribution of lifetimes of the positrons with annihilation by p-Ps, the distribution of lifetimes of the positrons with annihilation by o-Ps, the distribution of lifetimes of the positrons with direct (electron-positron) annihilation, and the distribution of lifetimes of the positrons in the sample (reference), as well as the fitting function.

An example of the distribution of lifetimes of positrons with annihilation by p-Ps is shown in FIG. 2. This distribution is characterised by the shortest mean positron lifetime and the narrowest distribution of lifetimes of positrons, as shown in FIG. 2. Regardless of the type of annihilation medium, i.e. the material in which the annihilation occurred, this time will be the shortest. The p-Ps distribution extracted is the narrowest among all extracted distributions, while the results calculated based on it will generally have the smallest uncertainty.

Therefore, extracting the distribution of lifetimes of p-Ps from the obtained distributions of lifetimes, and proceeding with subsequent calculations based on this distribution alone, allowed for, according to the developed method, to estimate the delay of each modules X of the TOF-PET detector more accurately than with the calculations taking into account complete distributions of lifetimes of positrons, which are graphically wide and therefore result in high uncertainty of the results.

The developed method, in turn, provides for calibration constants derived from data of distribution of lifetimes of p-Ps that involve lower uncertainty of results, which ultimately results in an improved quality of reconstructed images obtained using the TOF-PET scanner, in which the detection system is being calibrated according to the inventive method. Furthermore, in the developed method, an additional de-excitation quantum is used to determine the lifetime of positrons ($T_{Diff}$). The data from the recording of the de-excitation quantum allow for determining when the positronium ($T_{deex}$) was created, while the data on the annihilation time ($T_{anni}$) is obtained by measuring the annihilation quanta.

In order to determine the calibration constants based on the extracted distribution of lifetimes of p-Ps, i.e. positrons with annihilation by p-Ps, the maximum distribution of lifetimes of p-Ps (MaxLF) is defined as a measure of the position of said distribution for annihilation quanta and de-excitation quanta—for the module X of the detector system being calibrated, wherein the difference of said measures are determined using Formula V and Formula VI, according to Formula VII:

$$\text{MaxLF}_{anni}^{(X)} - \text{MaxLF}_{deex}^{(X)} = T_{Diff}^{(1)} - T_{Diff}^{(2)} = 2 \cdot D_{delay}^{(X)} \qquad \text{Formula VII}$$

where:

$\text{MaxLF}_{anni}^{(X)}$—maximum distribution of lifetimes of p-Ps based on the data for annihilation quanta recorded by detector X $\text{MaxL}_{deex}^{(X)}$—maximum distribution of lifetimes of p-Ps based on the data for de-excitation quanta recorded by detector X.

Formula VII is used to determine the delay of the module X being calibrated by analysing only the position of the maximum distribution of lifetimes of p-Ps $\text{MaxLF}_{anni}^{(X)}$ and $\text{MaxLF}_{deex}^{(X)}$ of said detector X.

By transforming Formula VII, a time constant is obtained that defines the delay of detector X, according to the following equation (Formula VIII):

$$D_{delay}^{(X)} = \frac{\text{MaxLF}_{anni}^{(X)} - \text{MaxLF}_{deex}^{(X)}}{2} \qquad \text{Formula VIII}$$

Maximum distribution of lifetimes of p-Ps: $\text{MaxLF}_{anni}^{(X)}$ and $\text{MaxLF}_{deex}^{(X)}$ can be determined by known methods, including for example by calculating the zero point of the first derivative function of each distribution or by fitting peak function. The width of the obtained maximum distribution of lifetimes of p-Ps (FIG. 2) depends on the time resolution of the detector. Moreover, the developed calibration method allows for using a material to be used as a positron shielding, which additionally shortens the lifetime of positrons, including those with annihilation by p-Ps, so that the distributions of lifetimes of p-Ps extracted are narrower, which translates into a reduced uncertainty of the obtained results, or more accurate estimation of the relative delay of each of the modules X being calibrated. Where the obtained value of the maximum distribution of lifetimes of p-Ps of one of the detection modules differs significantly from the value of the average maximum position for the other modules, a calibration correction calculated according to Formula VIII is implemented for said module. The wording 'a value that differs significantly' means that said value differs from the average maximum position for the other modules by at least one magnitude of uncertainty. This is because the above is assessed based on the uncertainty of the determination of the maximum value, which in turn depends on the resolution of the apparatus.

The absolute timing calibration of the entire TOF-PET detection system can therefore be performed by placing the radiotracer in the scintillation chamber of the TOF-PET scanner at a given position whose coordinates are known or by administering the radiotracer in the form of a radiopharmaceutical to the patient. Once a sufficient number of data from the events discussed in detail above is gathered, distributions of lifetimes of positrons are carried out, independently for each detection module, assuming each detection module to be module X, and then, following the decomposition of the distributions of lifetimes of positrons, the distributions of lifetimes of p-Ps are extracted, and the calibration constants, independently for each module X, are determined. FIG. 2 shows an example result of decomposition of the distribution of lifetimes—for one detection module X. As can be seen from FIG. 2, the distribution of lifetime of p-Ps is narrower than the distribution of lifetime of positrons with direct annihilation: of positron with electron in a reference material (reference). Furthermore, the distribution of lifetimes of o-Ps (positrons annihilated by o-Ps) contributes to the entire distribution of lifetimes of positrons becoming significantly more extensive, which may increase the uncertainty of the calibration procedure of the TOF-PET detection modules when such a distribution providing for o-Ps, is used in calculations.

Figure 4:
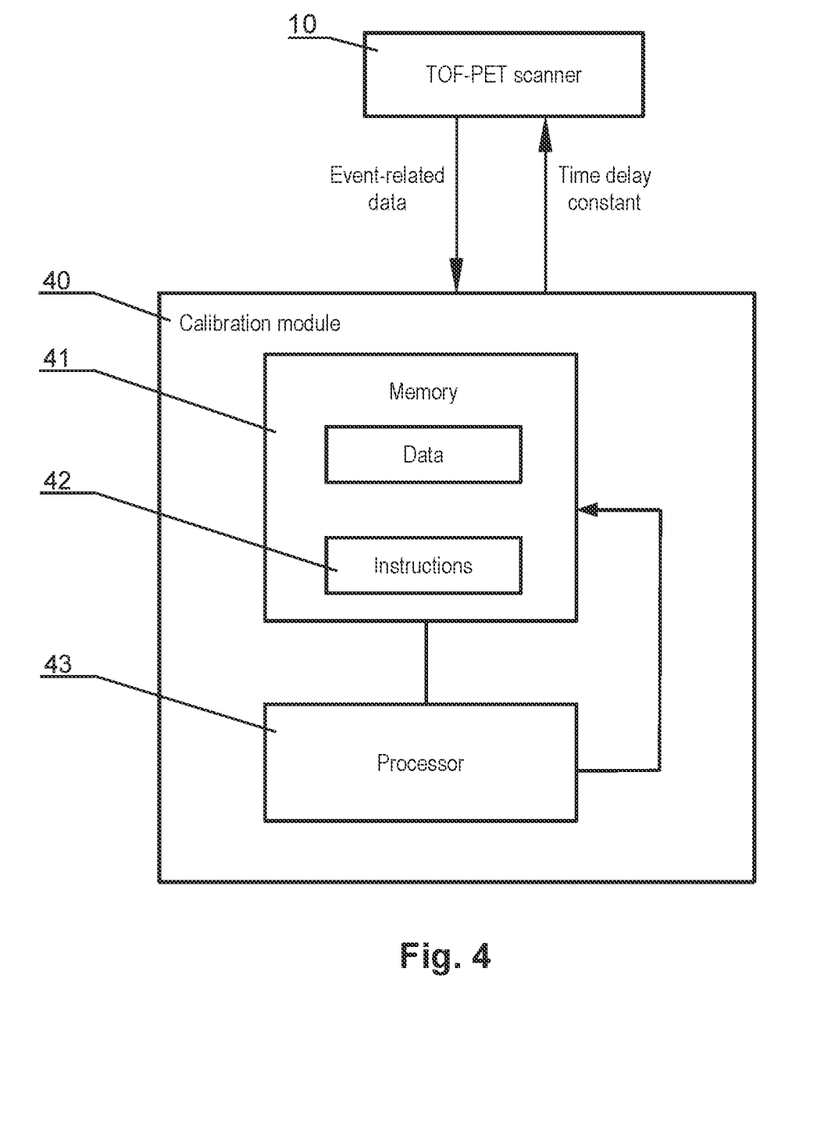
FIG. 4 shows the structure of a computer system for the implementation of the timing calibration procedure of the TOF-PET scanner detection system.

FIG. 4 shows an embodiment of a system for implementing the method according to the invention. This system cooperates with the components of the TOF-PET 10 scanner described in FIG. 1A-1D. The main component of the system is the calibration module 40 for carrying out calibrations according to the procedure described in FIG. 3. The module 40 may be implemented as a computer system comprising a memory 41, which has provided separate space for data and programme instructions 42 (for implementing the individual steps of the procedure discussed in FIG. 3), and a processor 43 connected to a storage 41 for executing programme instructions. The calibration data (i.e. the time delay constant ($D_{delay}^{(X)}$) for each detection module (X) being calibrated) are transferred to the TOF-PET 10 scanner.

The invention claimed is:

1. A method for a TOF-PET scanner, the TOF-PET scanner comprising a scintillation chamber and a detection system, the detection system comprising detection modules (X) that surround the scintillation chamber; the method comprising:

providing a radiation source in the scintillation chamber, wherein the radiation source is configured to emit, in the scintillation chamber, both positrons for annihilation with emission of annihilation quanta and de-excitation quanta having an energy different from an energy of the annihilation quanta;

registering the annihilation quanta deposited in the detection modules (X) as registered annihilation quanta and the de-excitation quanta deposited in the detection modules (X) as registered de-excitation quanta;

selecting the registered annihilation quanta and the registered de-excitation quanta based on times of registration and energies of the deposited quanta;

assigning the annihilation quanta and the de-excitation quanta to common events;

wherein the method further comprises, for each detection module (X) being calibrated:

determining distributions of lifetimes of positrons based on differences of the times of registration of annihilation quanta and of the times of registration of the de-excitation quanta assigned to the common events and registered by the module being calibrated;

extracting, from the determined distributions of lifetimes of positions, a distribution of lifetimes of positrons with annihilation by para-positronium; and determining a time delay constant based on the extracted distributions of lifetimes of positrons with annihilation by a para-positronium.

2. The method according to claim 1, comprising determining the time delay constant for the detection module being calibrated relative to a virtual detection module having a time delay constant equal to an average delay value of the time delay constants of all the detection modules of the detection system, except for the detection module being calibrated.

3. The method according to claim 2, wherein a value of the time delay constant of the virtual detection module is assumed to be zero.

4. The method according to claim 1, comprising determining the distributions of lifetimes of positrons for the detection module being calibrated by:

calculating a positron lifetime for the events in which the detection module being calibrated has registered the annihilation quantum, according to a formula:

$$T_{Diff}^{(1)} = (T_{anni}^{(X)} - T_{deex}) + D_{delay}^{(X)}, \quad \text{(Formula V)}$$

and calculating a positron lifetime for the events in which the detection module being calibrated has registered the de-excitation quantum, according to a formula:

$$T_{Diff}^{(2)} = (T_{anni} - T_{deex}^{(X)}) - D_{delay}^{(X)}, \quad \text{(Formula VI)}$$

wherein:

$T_{anni}^{(X)}$ is a time of registration of the annihilation quantum in the detection module being calibrated $T_{deex}$ is a time of registration of the de-excitation quantum originating from the common event with the annihilation quantum of the time of registration, $T_{deex}^{(X)}$ is a time of registration of the de-excitation quantum in the detection module being calibrated, $T_{anni}$ is a time of registration of the annihilation quantum originating from the common event with the de-excitation quantum of time of registration, $D_{delay}^{(X)}$ is a time constant defining a delay of the detection module being calibrated, and, based on obtained calculating results, determining the distributions of the lifetimes of positrons for the detection module being calibrated as a function of a number of counts of said events.

5. The method according to claim 4, comprising determining the time delay constant of the detection module being calibrated by:
extracting the distributions of lifetimes of positrons with annihilation by the para-positronium, from the distributions of lifetimes of positrons as extracted distributions,
and next, determining maxima of the extracted distributions of lifetimes of positrons, including calculating mutual displacement of said maxima and determining a time constant defining the delay of the detection module being calibrated according to a formula:

$$D_{delay}^{(X)} = \frac{\text{Max}LF_{anni}^{(X)} - \text{Max}LF_{deex}^{(X)}}{2} \quad \text{(Formula VIII)}$$

wherein:
$\text{MaxLF}_{anni}^{(X)}$ is a maximum distribution of lifetimes of p-Ps $n_1=f(T_{ani(p-Ps)}^{(X)}$ extracted from distribution $n1=f(T_{Diff}^{(1)})$
$\text{MaxL}_{deex}^{(X)}$ is a maximum distribution of lifetimes of p-Ps $n_2=f(T_{deex(p-Ps)}^{(X)})$ extracted from $n2=f(T_{Diff}^{(2)})$.

6. The method according to claim 1, comprising carrying out the calibration of the detection system of the TOF-PET scanner with a time resolution necessary to extract the distribution of lifetimes of positrons with annihilation by p-Ps with a mean lifetime of not more than 125 ps.

7. The method according to claim 1, comprising carrying out the calibration of the detection system of the TOF-PET scanner of the time resolution of at least 100 ps.

8. The method according to claim 1, comprising carrying out the calibration of the detection system of the TOF-PET scanner comprising polymer scintillation strips as working material for deposition of annihilation and de-excitation quanta.

9. The method according to claim 1, comprising carrying out the calibration with a use of a shielding material for reducing the lifetime of positrons ($T_{Diff}$, $T_{Diff}^{(1)}$, $T_{Diff}^{(2)}$).

10. The method according to claim 1, comprising providing the radiation source in a form of at least one isotope selected from a group consisting of: $^{14}$O, $^{22}$Na and $^{44}$Sc.

11. A calibration system for a TOF-PET scanner, the TOF-PET scanner comprising a scintillation chamber and a detection system, the detection system comprising detection modules (X) that surround the scintillation chamber; the calibration system comprising:

a radiation source for placement in the scintillation chamber, wherein the radiation source is configured to emit, in the scintillation chamber, both positrons for annihilation with emission of annihilation quanta and de-excitation quanta having an energy different from an energy of the annihilation quanta;

wherein the detection system is configured to register the annihilation quanta deposited in the detection modules (X) as registered annihilation quanta and the de-excitation quanta deposited in the detection modules (X) as registered de-excitation quanta;

a calibration module configured to select the registered annihilation quanta and the registered de-excitation quanta based on times of registration and energies pf of the deposited quanta and to assign the annihilation quanta and the de-excitation quanta to common events; wherein the calibration module is further configured to, for each detection module being calibrated:

determine distributions of lifetimes of positions based on a differences of the times of registration of annihilation quanta and of times of registration of the de-excitation quanta assigned to the common events and registered by the module being calibrated;

extract, from the determined distributions of lifetimes of positrons, a distribution of lifetimes of positrons with annihilation by para-positronium; and determine a time delay constant based on the extracted distributions of lifetimes of positrons with annihilation by para-positronium.

* * * * *